United States Patent [19]
Heck

[11] 3,988,358
[45] Oct. 26, 1976

[54] PROCESS FOR THE PREPARATION OF CARBOXYLIC ACID ESTERS FROM ORGANIC HALIDES

[75] Inventor: Richard F. Heck, Wilmington, Del.

[73] Assignee: The University of Delaware, Newark, Del.

[22] Filed: May 10, 1974

[21] Appl. No.: 468,762

[52] U.S. Cl. .................. 260/465 D; 260/293.86; 260/485 G; 260/295 R; 260/486 AC; 260/295 AM; 260/514 L; 260/295.5 A; 260/514 K; 260/326.5 E; 260/515 R; 260/332.2 R; 260/515 P; 260/332.2 C; 260/515 A; 260/410.5; 260/518 R; 260/410.6; 260/521 R; 260/410.9 R; 260/413; 260/526 N; 260/468 L; 260/557 R; 260/468 K; 260/558 R; 260/469; 260/558 P; 260/471 R; 260/558 A; 260/471 A; 260/558 D; 260/559 R; 260/472; 260/559 S; 260/473 R; 260/561 N; 260/473 S; 260/562 R; 260/521 B; 260/475 R; 260/475 F; 260/475 PN; 260/475 P; 260/476 R; 260/477; 260/479 R; 260/479 S; 260/482 R; 260/485 R; 260/485 L; 260/485 H

[51] Int. Cl.² ............... C07C 67/36; C07C 69/54; C07C 69/78; C07C 121/52

[58] Field of Search ........ 260/488 K, 493, 486 AC, 260/468 L, 468 K, 476 R, 477, 465 D, 473 R, 473 S, 479 R, 479 S, 475 R, 475 PN, 475 F, 475 P, 295.5 R, 295 R, 332.2 C, 469, 485 R, 485 L, 485 H, 485 G, 410.5, 410.6, 410.9 R, 471 R, 471 A, 472

[56] References Cited

UNITED STATES PATENTS 3,626,005  12/1971  Scheben et al. ............ 260/486 AC

OTHER PUBLICATIONS

Heck et al., J.A.C.S. 85, pp. 2779–2782 (1963).
Falbe, Carbon Monoxide in Organic Synthesis pp. 118–120 (1970).

*Primary Examiner*—Jane S. Myers

[57] ABSTRACT

Carboxylic acid esters or amides are obtained from aryl, heterocyclic, vinylic, ethynylic, and benzylic halides and substituted derivatives thereof, by reacting same with an alcohol or primary or secondary amine and carbon monoxide, in the presence of a palladium catalyst and if necessary a tertiary amine at about 20°–150° C and from about a half to about 100 atmospheres pressure. A typical example is the conversion of bromobenzene into n-butyl benzoate at 100° C and one atmosphere of carbon monoxide in the presence of tri-n-butyl-amine and a catalytic amount of $PdBr_2[P(C_6H_5)_3]_2$.

8 Claims, No Drawings

PROCESS FOR THE PREPARATION OF CARBOXYLIC ACID ESTERS FROM ORGANIC HALIDES

The Government has rights in this invention pursuant to Grant No. 73-75-GP-34492X awarded by the National Science Foundation.

This invention relates to a catalytic process for the preparation of carboxylic acid esters and amides from organic halides.

It is known that allylic chlorides can be converted in poor yield into methyl 3-butenoate derivatives with a palladium catalyst, carbon monoxide and methanol (e.g., D. Medema, R. vanHelden and C. F. Kohll, *Inorg. Chim. Acta*, 3, 255 (1969)). Allylic chlorides are also well known to be very reactive halides and to form isolatable complexes with palladium, π-allylpalladium chloride dimers. This carboxylation reaction is applicable only to the very reactive allylic halides, however.

It is the object of this invention to catalytically produce carboxylic esters and amides in good yields under mild conditions from organic halides other than allylic halides, including those organic halides that have been considered to be unreactive as compared to allylic halides.

In accordance with the present invention it has been found that carboxylic esters or amides are produced when aryl, heterocyclic, vinylic, ethynylic or benzylic halides or substituted derivatives thereof are in contact with carbon monoxide, and an alcohol (if esters are to be produced) or a primary or secondary amine (if amides are to be produced), in the presence of a palladium catalyst and if necessary a tertiary amine.

The process of this invention appears to depend upon the reactions broadly expressed as follows:

$$RX + PdL_n \rightleftharpoons RPdL_2X + (n-2)L$$

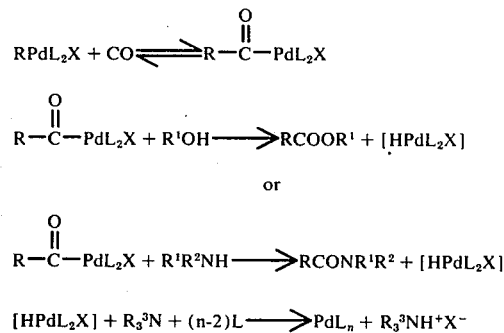

$$[HPdL_2X] + R_3N + (n-2)L \longrightarrow PdL_n + R_3NH^+X^-$$

in which R is an aryl, heterocyclic, vinylic, ethynylic or benzylic group or substituted derivates thereof, X is iodide, bromide or chloride, L is a coordinating group such as triphenylphosphine where n is 2, 3 or 4, $R^1$ is an aryl, alkyl, cycloalkyl, benzylic or a hydrogen group, $R^2$ may be the same as $R^1$ or it may be attached to $R^1$ to form cyclic groups, and $R^3$ is a lower alkyl group, hydrogen, or a cycloalkyl group or two of the $R^3$ groups may be joined to form a ring and the third $R^3$ group would be a lower alkyl, hydrogen or a cycloalkyl group.

The R, $R^1$ and $R^2$ groups as defined above may also have various substituents present such as alkyl and aryl groups, cycloalkyl groups, nitro, cyano, ester, carboxylate, amide, aldehyde and even hydroxylic, amino or substituted amino and halogen groups if these groups are less reactive than the other groups in the reactants which are intended to take part in the reaction.

Examples of organic halides, RX, which will undergo the reaction of this invention are bromobenzene, iodobenzene, p-acetoxyiodobenzene, methyl p-bromobenzoate, p-bromobenzonitrile, o-iodobenzoic acid, p-bromoanisole, m-bromoacetophenone, p-iodophenol, p-chlorobromobenzene, 3-bromopyridine, 2-bromothiophene, benzyl chloride, 2-bromonaphthalene, p-methoxybenzyl chloride, vinyl bromide, bromoacetylene, 1-bromostyrene, 2-bromostyrene, 2-bromopropene, 2-chloropropene, 1-bromocyclohexene, methyl 3-bromoacrylate, 3-iodobenzaldehyde, bromophenanthrene, 3-iodo-3-hexene, 1-bromohexyne, m-iodoaniline and 1,2 and 1,4-dibromobenzene.

The coordinating group L is usually triphenylphosphine although other phosphine derivatives such as triethylphosphine, tri-n-butylphosphine, tri-p-anisylphosphine, tri-o-tolylphosphine, trimethyl phosphite and triphenyl phosphite may also be used. In some instances with the more reactive RX molecules, particularly iodides, the phosphine derivative may not be necessary at all in which case L becomes a solvent group or a group of one of the other reactants present in the reaction mixture.

In the cases where esters are being produced $R^1OH$ may be an alcohol or a phenol such as: methanol, ethanol, propanol, n-butanol, 2-butanol, amyl alcohol, 1-dodecanol, cyclohexanol, benzyl alcohol, 2-phenylethanol, ethylene glycol, glycerol, phenol, p-methoxyphenol, p-cresol, methyl hydroxyacetate, 2-diethylaminoethanol, tripropanolamine and alpha-naphthol.

When amides are desired instead of esters $R^1R^2NH$ is used instead of $R^1OH$. Examples of $R^1R^2NH$ which may be used are: ammonia, methylamine, dimethylamine, diethylamine, n-propylamine, n-butylamine, cyclohexylamine, aminothiophene, naphthylamine, aniline, N-methylaniline, p-nitroaniline, p-methoxyaniline, pyrrolidine, piperidine, p-phenylenediamine, methyl glycinate, benzylamine, p-carbomethoxybenzylamine, and ethylenediamine.

A basic tertiary amine is usually necessary to make the reaction catalytic in palladium. If the amide producing reaction is carried out with a strongly basic primary or secondary amine it is not necessary to add the tertiary amine, however, but two equivalents of the primary or secondary amine relative to the halide, RX, are then used instead of one. Examples of tertiary amines which can be used are: triethylamine, tri-n-butylamine, triisopropylamine, tetramethylethylenediamine, N-methylpiperidine, N,N-di-cyclohexylethylamine, benzyldiethylamine dimethylisopropylamine and tri-n-propylamine.

If water is used as the reactant ($R^1=H$) then another equivalent of tertiary amine must also be added to neutralize the carboxylic acid product formed. Similarly if acidic phenols are used as the reactants excess tertiary amine is advantageous in keeping the solution basic and giving higher yields of the phenolic esters than are obtained with only equivalent amounts of amine.

The process of this reaction is carried out at a temperature in the range of 20° C to about 175° C with a carbon monoxide pressure of about one half an atmosphere to about 100 or more atmospheres. The preferred temperatures are about 50°–160° with a pressure of about one to 10 atmospheres of carbon monoxide.

Generally no solvent is necessary for the reaction if the reactant mixture is liquid at the reaction temperature. Solvents such as excess reactant amine, excess reactant alcohol, tetrahydrofuran, toluene, N-methylpyrrolidone and dimethylformamide may be used, however, with little effect upon the reaction.

The ratios of reactants used is not critical. The organic halide, RX, may be the limiting reagent in which case a 5–100 percent or more excess of the alcohol or primary or secondary amine is used. The reaction may be carried out equally well with equivalent or excess amounts of the organic halides. The tertiary amine is added in amounts equivalent to or in excess of the organic halide.

Catalyst concentrations of from about 0.01 mole percent to about 10. mole percent or more may be used with about 0.1 to 2% being generally preferred. The catalyst may be added as finely divided palladium metal in cases where the RX is an iodide but in other cases palladium(II) salts are preferred such as the dihalides or the diacetate. In the last cases the catalyst usually must be used in conjunction with a triorganic phosphine or phosphite in which cases triorganophosphine or triorganophosphite palladium complexes are formed under the reaction conditions. While ratios of two phosphines per palladium are generally sufficient higher ratios of up to 30 or more to one are sometimes advantageous in allowing higher steriospecificity to be obtained in the ester producing reaction from cis-vinylic halides.

The following examples illustrate various ramifications of this invention, but the invention is not to be limited thereby.

EXAMPLE 1

A mixture of 17.2 mmoles of iodobenzene, 21.2 moles of n-butanol, 19 mmoles tri-n-butylamine and 0.25 mmoles palladium acetate was stirred magnetically under one atmosphere of carbon monoxide at 100° under gas absorption stopped (about 20 hours). After cooling the ester was extracted from the reaction mixture with ether and the excess amine and amine salt were removed by washing the extract with aqueous hydrochloric acid. After drying and distilling there was obtained a 70% yield of n-butyl benzoate, b.p. 100°–110° (10 mm.).

EXAMPLE 2

A reaction was carried out as in Example 1 using methyl p-iodobenzoate in place of iodobenzene and n-butyl methyl terephthalate was obtained in 83% yield, b.p. 133°–134° (0.2mm.).

EXAMPLE 3

A reaction was carried out as in Example 1 using p-iodoanisole instead of iodobenzene and n-butyl p-methoxybenzoate was produced in 69% yield, b.p. 114°–115° (0.2 mm.).

EXAMPLE 4

A reaction was carried out as in Example 1 using 2,6-dimethyliodobenzene instead of iodobenzene and n-butyl 2,6-dimethylbenzoate was obtained in 63% yield, b.p. 78°–80° (0.4 mm.).

EXAMPLE 5

A reaction was carried out as in Example 1 except that iodo(bistriphenylphosphine)phenylpalladium (0.25 mmoles) was used in place of palladium acetate. There was obtained n-butyl benzoate in 96% yield as determined by vapor phase chromatography.

EXAMPLE 6

A mixture of 17.2 mmoles of bromobenzene, 21.2 mmoles n-butanol, 19 mmols tri-n-butylamine and 0.25 mmole of bromo(bistriphenylphosphine)phenylpalladium was reacted at 100° under one atmosphere of carbon monoxide until gas absorption stopped (about 24 hours). Isolation of the product as in Example 1 gave n-butyl benzoate in 78% yield.

EXAMPLE 7

A reaction was carried out as in Example 6 employing 0.125 mmole dibromo-$\mu,\mu$-dibromobistriphenylphosphinepalladium as catalyst instead of 0.25 mmole of bromo(bistriphenylphosphine)phenylpalladium. There was obtained n-butyl benzoate in good yield.

EXAMPLE 8

In a 200 ml pressure vessel was placed 17.2 mmoles p-bromobenzonitrile, 21.2 mmoles n-butanol, 19 mmoles tri-n-butylamine and 0.25 mmole dibromo(bistriphenylphosphine) palladium. The vessel was flushed with carbon monoxide and pressured to 30 psig. and the reaction mixture was stirred at 60° for 14 hours. Isolation of the product as in Example 1 gave 89% of n-butyl p-cyanobenzoate, m.p. 54°–55°.

EXAMPLE 9

An example was carried out as in Example 1 with 1-bromonaphthalene in place of iodobenzene and dibromo(bistriphenylphoshine)palladium as the catalyst. After 80 hours at 100° there was obtained n-butyl 1-naphthoate in 46% yield, b.p. 165°–170° (19 mm.).

EXAMPLE 10

A reaction was carried out as in Example 1 using benzyl chloride instead of iodobenzene and dichloro(bistriphenylphosphine)palladium as the catalyst. After 40 hours at 100° there was isolated n-butyl phenylacetate in 45% yield, b.p. 135°–142° (22 mm.).

EXAMPLE 11

A reaction was carried out as in Example 8 with methanol used in place of n-butanol. There was obtained in good yield methyl p-cyanobenzoate.

EXAMPLE 12

A reaction was carried out as in Example 8 with cyclohexanol instead of n-butanol and bromobenzene instead of p-bromobenzonitrile. Cyclohexyl benzoate was obtained.

EXAMPLE 13

An example was carried out as described in Example 12 using ethanol instead of cyclohexanol and ethyl benzoate was obtained.

EXAMPLE 14

A mixture of 17.2 mmoles cis-3-iodo-3-hexene, 21.2 mmoles n-butanol, 17 mmoles tri-n-butylamine and 0.25 mmoles diiodo(bistriphenylphosphine)palladium was stirred at 60° under one atmosphere of carbon monoxide for 40 hours. There was obtained from the reaction mixture 74% of cis and 6% of trans n-butyl 3-hexenecarboxylate.

EXAMPLE 15

A reaction was carried out as in Example 14 using cis-1-iodo-1-hexene in place of cis-3-iodo-3-hexene. After 1.5 hours at 80° there was produced 79% of cis n-butyl 2-heptenoate and 6% of the trans ester.

EXAMPLE 16

A reaction was carried out as in Example 14 with trans-1-iodo-1-hexene. After 2 hours at 100° there was formed an 83% yield of trans n-butyl 2-heptenoate.

EXAMPLE 17

A reaction similar to the one described in Example 14 was carried out with trans-2-bromostyrene using dibromo(bistriphenylphosphine)palladium as catalyst. After eight hours reaction time at 100° there was produced an 80% yield of trans n-butyl cinnamate.

EXAMPLE 18

The procedure of Example 17 was used employing cis-2-bromostyrene instead of the trans isomer. After 43 hours at 60° there was formed a 68% yield of cis n-butyl cinnamate and 16% of the trans ester.

EXAMPLE 19

A reaction as in Example 14 was carried out using 1-bromostyrene instead of 3-iodo-3-hexane and dibromo(bistriphenylphosphine)palladium was used as the catalyst. In 5 hours at 100° there was produced a 68% yield of n-butyl 2-phenylacrylate, b.p. 90°–105° (1.5 mm.).

EXAMPLE 20

A reaction was carried out as in Example 14 with 1-iodo-1-hexyne in place of iodobenzene. At room temperature, methyl 2-heptynoate was formed in a few hours.

EXAMPLE 21

A reaction was carried out as in Example 6 except that 38 mmoles of aniline was added instead of 21.2 mmoles of n-butanol. After 3.5 hours reaction at 100° the reaction mixture was cooled and extracted with ether. The extracts were washed with dilute aqueous acid, dried and concentrated. On cooling the solution deposited a 94% yield of colorless crystals of N-phenylbenzamide, m.p. 162.5°–163°.

EXAMPLE 22

Example 21 was carried out with 25 mmoles of benzylamine instead of aniline and there was produced N-benzylbenzamide in 79% yield, m.p. 105°–105.5°.

EXAMPLE 23

Example 21 was carried out with methyl p-bromobenzoate instead of bromobenzene and in 3 hours at 100° there was produced N-phenyl-p-carbomethoxybenzamide in 86% yield, m.p. 192°–193°.

EXAMPLE 24

Example 21 was carried out with p-bromoanisole instead of bromobenzene. After 10 hours reaction time at 100° there was obtained a 76% yield of p-methoxybenzamide, m.p. 173°–174°.

EXAMPLE 25

Example 21 was carried out with p-bromonitrobenzene instead of bromobenzene. After 3.5 hours at 100° there was formed p-nitrobenzamide in 57% yield, m.p. 211°–212°.

EXAMPLE 26

Example 21 was carried out with 3-bromopyridine instead of bromobenzene and N-phenylnicotinamide was formed in 50% yield, m.p. 118°–119°.

EXAMPLE 27

Example 21 was carried out with 2-bromothiophene rather than bromobenzene and N-phenyl-2-thiophenecarboxamide was formed in 63% yield, m.p. 139°–149°.

EXAMPLE 28

A mixture of 17.2 mmoles of trans-2-bromostyrene, 50 mmoles of pyrrolidine and 0.25 mmole dibromo(bistriphenylphosphine)-palladium was heated at 60° for 2.5 hours under one atmosphere of carbon monoxide. Trans-n-Cinnamoylpyrrolidine was isolated from the reaction mixture in 91% yield (m.p. 100°–100.5°).

EXAMPLE 29

Example 27 was carried out with cis-2-bromostyrene in place of the trans isomer and with 25 mmoles of aniline and 19 mmoles of tri-n-butylamine rather than with pyrrolidine. After 4 hours at 60° there was isolated from the reaction mixture an 80% yield of cis-N-phenyl-cinnamamide, m.p. 101°–102°.

EXAMPLE 30

A mixture of 17.2 mmoles cis-3-iodo-3-hexene, 25 mmoles aniline, 19 mmoles tri-n-butylamine and 0.25 mmoles of diiodo(bistriphenylphosphine)palladium was heated and stirred for 1.5 hours at 100° under one atmosphere pressure of carbon monoxide. From the reaction mixture there was isolated a 71% yield of cis-N-phenyl-3-hexene-3-carboxamide, m.p. 96°–97°.

EXAMPLE 31

A reaction was carried out as in Example 29 using E-methyl 3-bromo-2-methylpropenoate instead of cis-3-iodo-3-hexene and dibromo(bistriphenylphosphine)-palladium as catalyst. After two hours reaction at 100° there was obtained E-N-phenyl-2-carbomethoxy-2-butenamide in 80% yield.

EXAMPLE 32

Example 21 was carried out with 3-bromopyridine instead of bromobenzene and with ammonia instead of aniline in a pressure vessel with 1000 psig. of carbon monoxide at 100°. There was obtained nicotinamide as a product.

EXAMPLE 33

A mixture of 100 mmoles 2-chloropropene, 25 mmoles aniline, 30 mmoles tri-n-butylamine and 0.2 mmoles $PdCl_2(P\phi_3)_2$ was stirred magnetically in a pressure vessel under 800 psig. of carbon monoxide, at 140° for 12 hours. The gas pressure dropped to about 400 psi. during this time. There was obtained from the reaction mixture a 74% yield of N-phenylmethacrylamide, m.p. 84°–85°.

EXAMPLE 34

A reaction was carried out as in Example 33 and methanol was used in place of aniline. The product was methyl methacrylate.

As can be seen from the above examples this invention is broadly applicable to a wide variety of organic halides. The products produced by it are valuable compounds used either as chemical intermediates or directly, for example, in the synthetic fiber industry, pharmaceutical or perfumery and flavoring industries. Phthalate esters, for example, could be produced from o-dihalobenzenes for use as plasticizers. Terephthalate esters could be formed from p-dihalobenzenes for use in making polytheylene terephthalate. Esters of benzoic acids and cinnamic acids are widely used in the perfume industry and can be made as shown in the examples. Amides are used in the pharmaceutical industry. The amide of nicotinic acid for example is a B vitamin and it can be made from 3-bromo-pyridine by the procedure disclosed herein. Furthermore, this invention is generally very simple to use because it often does not require elaborate equipment, high temperatures or high pressures. The catalyst is not only highly effective but also is non-volatile and presents no health hazard to use.

As many apparently widely different embodiments of this invention may be made without departing from the spirit and scope thereof, it is to be understood that this invention is not limited to the specific embodiments thereof except as defined in the appended claims.

I claim:

1. The catalytic process of producing esters from aryl, heterocyclic, benzylic, vinylic and ethynylic halides, which comprises reacting said halide with an alcohol and carbon monoxide in the presence of a palladium catalyst selected from the group consisting of palladium metal and a palladium complex reducible to palladium in the zero valent state under the reaction condition and in the presence of a basic tertiary amine in a molar equivalent amount compared to the halide or in excess of that amount, said reaction being carried out at a temperature within the range of from 20° C to 175° C and at a pressure of about a half an atmosphere to 1000 atmospheres.

2. The process of claim 1 in which the palladium complex is a triorganophosphorus complex and is either added as catalyst or such a complex is formed under the reaction conditions by adding the triorganophosphorus compound and palladium metal or a palladium salt.

3. The process of claim 1 wherein the halides are aryl, heterocyclic, and vinylic halides, the catalyst is a triorganophosphine complex of a palladium halide or a combination of reagents which produces such a complex.

4. The process of claim 3 in which the halides are vinylic chlorides or bromides and the products are $\alpha,\beta$-unsaturated esters.

5. The process of claim 3 where the halide is 2-chloropropene and the alcohol is methanol producing methyl methacrylate.

6. The process of claim 3 in which the aryl, heterocyclic and vinylic halides are bromides.

7. The process of claim 6 in which the triorganophosphine is a triarylphosphine.

8. The process of claim 7 in which aryl bromides and alcohols are reacted to product benzoate or substituted benzoate esters.

* * * * *